US009327058B2

(12) United States Patent
Isch

(10) Patent No.: US 9,327,058 B2
(45) Date of Patent: May 3, 2016

(54) HYDROGEL ENHANCED MEDICAL DEVICES

(75) Inventor: Andrew P. Isch, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 508 days.

(21) Appl. No.: 13/382,348

(22) PCT Filed: Jul. 7, 2010

(86) PCT No.: PCT/US2010/041181
§ 371 (c)(1),
(2), (4) Date: Jan. 31, 2012

(87) PCT Pub. No.: WO2011/005840
PCT Pub. Date: Mar. 13, 2011

(65) Prior Publication Data
US 2012/0123527 A1 May 17, 2012

Related U.S. Application Data

(60) Provisional application No. 61/223,418, filed on Jul. 7, 2009.

(51) Int. Cl.
A61F 2/82 (2013.01)
A61L 31/06 (2006.01)
A61L 31/10 (2006.01)
A61L 31/14 (2006.01)

(52) U.S. Cl.
CPC ............ A61L 31/06 (2013.01); A61L 31/10 (2013.01); A61L 31/145 (2013.01)

(58) Field of Classification Search
CPC ........................................... A61F 2/82
USPC ................................................ 623/1.35
See application file for complete search history.

(56) References Cited

U.S. PATENT DOCUMENTS

| | | | |
|---|---|---|---|
| 3,975,350 A | 8/1976 | Hudgin et al. | |
| 4,424,305 A | 1/1984 | Gould et al. | |
| 4,705,709 A | 11/1987 | Vailancourt | |
| 4,789,720 A | 12/1988 | Teffenhart | |
| 4,798,876 A | 1/1989 | Gould et al. | |
| 4,810,582 A | 3/1989 | Gould et al. | |
| 4,883,699 A | 11/1989 | Aniuk et al. | |
| 4,990,357 A | 2/1991 | Karakelle et al. | |
| 5,015,238 A | 5/1991 | Solomon et al. | |
| 5,061,254 A | 10/1991 | Karakelle et al. | |
| 5,674,241 A | 10/1997 | Bley et al. | |
| 5,688,855 A * | 11/1997 | Stoy et al. ...................... | 524/505 |
| 5,800,412 A | 9/1998 | Zhang et al. | |

(Continued)

Primary Examiner — Thomas J Sweet
Assistant Examiner — Matthew Schall
(74) Attorney, Agent, or Firm — Brinks Gilson & Lione

(57) ABSTRACT

The present disclosure generally provides a stent-graft for insertion into a body vessel that comprises hydrophilic polyurethane hydrogel cuffs and an elongated cylindrical body. This stent-graft exhibits an enhanced ability to maintain its original position when placed into a patient and resist the potential of migration without causing excessive discomfort to the patient. Upon exposure to bodily fluids, the cuffs of the stent-graft expand to exert a sealing or anchoring force against the wall of the body vessel. Such a stent-graft overcomes many of the problems associated with conventional stent-grafts as currently used in many different applications, for example, endovascular repair and ureteral drainage.

9 Claims, 6 Drawing Sheets

(56) References Cited

U.S. PATENT DOCUMENTS

| | | |
|---|---|---|
| 5,902,329 A * | 5/1999 | Hoffmann et al. ............ 607/121 |
| 6,120,904 A | 9/2000 | Hostettler et al. |
| 6,265,016 B1 | 7/2001 | Hostettler et al. |
| 7,160,318 B2 | 1/2007 | Greenberg et al. |
| 7,175,652 B2 | 2/2007 | Cook et al. |
| 7,371,257 B2 | 5/2008 | Sahatjian et al. |
| 7,393,357 B2 | 7/2008 | Stelter et al. |
| 7,442,205 B2 | 10/2008 | Verhoeven et al. |
| 2004/0098097 A1 | 5/2004 | Fogarty et al. |
| 2004/0127978 A1 | 7/2004 | Sparer et al. |
| 2006/0247760 A1 | 11/2006 | Ganesan et al. |
| 2007/0179600 A1 | 8/2007 | Vardi |
| 2008/0249457 A1 | 10/2008 | Li et al. |
| 2009/0054845 A1 | 2/2009 | Puhasmagi et al. |

* cited by examiner

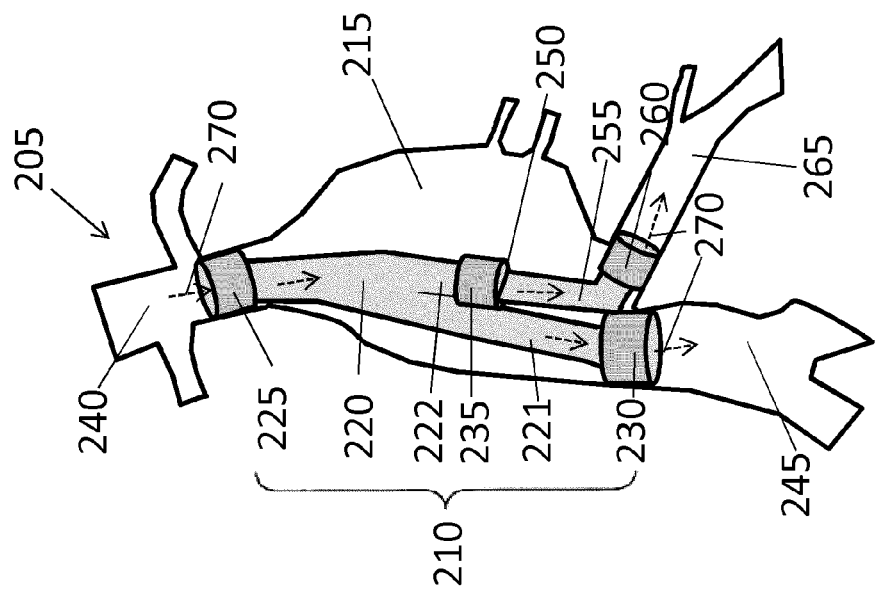
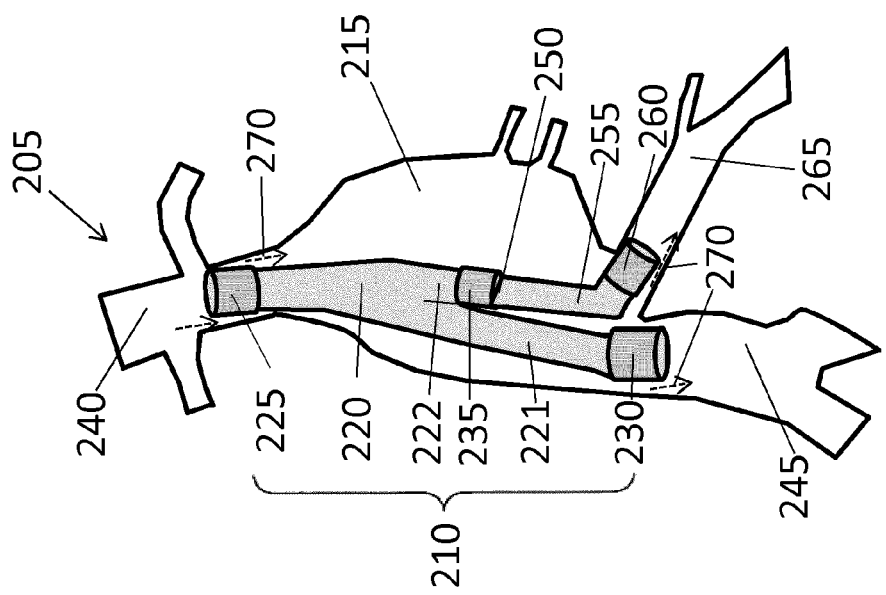

HYDROGEL ENHANCED MEDICAL DEVICES

CROSS REFERENCE TO RELATED APPLICATIONS

This application is related to and claims the benefit of priority to PCT/US2010/041181, filed on Jul. 7, 2010 which application claims the benefit of priority to U.S. Provisional Application Ser. No. 61/223,418 filed Jul. 7, 2009, the entire contents of which are hereby incorporated herein by reference.

FIELD

The present invention relates generally to implantable medical devices and more specifically to intraluminal stent or graft (stent-graft) prostheses.

BACKGROUND

Endovascular repair of an abdominal aortic aneurysm (AAA) is commonly performed using stent or graft (stent-graft) prostheses. Stent-graft prostheses can perform much like surgical grafts by bridging the dilated segment of an aneurysm, thereby, excluding it from direct blood flow. The purpose of stent-graft prostheses is to protect the excluded aneurysm from arterial pressure, dilatation, and rupture, while maintaining blood flow downstream. If any type of leakage occurs either at the site of interaction between the stent-graft and the bodily tissue, between any two components of the stent-graft, or through small perforations in the stent-graft, then the purpose of the stent-graft is defeated resulting in a continuation of the risk associated with rupturing. Although a stent-graft may be initially secured in place through the use of frictional forces or fixation barbs, migration of the stent-graft away from its original position exasperates the possibility of leakage. The only remedy for such an occurrence is early detection and re-intervention, e.g., repair by implanting a new stent-graft.

The treatment for a ureteral obstruction or fistula also commonly involves the use of stent-graft prostheses. The purpose of stent-graft prostheses in such an application is to provide urinary drainage from the renal pelvis of the kidney into the bladder. Similarly, stent-graft prostheses can be used to allow sufficient drainage from the liver through the biliary ducts, from the pancreas through the pancreatic ducts, and from the gall bladder through the bile ducts. Peristaltic action in the ureter often results in the migration and possibly even complete expulsion of the graft-stent from the ureter. In order to prevent migration, many ureteral stent-graft prostheses are provided with a curled extension located at the proximal and/or distal end. Unfortunately, the presence of such a curled end increases patient discomfort and irritation of the bladder or kidney.

SUMMARY

The present disclosure provides a stent-graft for insertion into a body vessel for use as or with a branch connection device that exhibits an enhanced ability to maintain its original position when placed into a patient and resist the potential of migration without causing excessive discomfort to the patient. One embodiment of a stent-graft, constructed in accordance with the teachings of the present invention, generally comprises a radially expandable cylindrical body having a proximal cuff, an elongated body, and a distal cuff. Each cuff and the elongated body have a substantially similar outer diameter, the elongated body having greater longitudinal length than the proximal and distal cuffs. A hydrophilic polyurethane hydrogel layer is disposed about at least one of the proximal and distal cuffs. Upon exposure to an aqueous environment, the polyurethane hydrogel expands so that the outer diameter of the cuff increases by about 10-30% and exerts a sealing force against the wall of the body vessel.

According to one aspect of the present invention, the expandable cylindrical body of the stent-graft may comprise more than one distal cuff in order to address the occurrence of a branch in the body vessel. The expandable cylindrical body being either modular or unibody in nature.

Another objective of the present disclosure is to provide method of repairing a ruptured or symptomatic defect in a body vessel having bodily fluids using a stent-graft. This method generally comprises the steps of selecting a stent-graft as described above that includes proximal and distal cuffs each having a "dried" polyurethane hydrogel layer disposed about it; inserting the stent-graft into the body vessel; positioning the proximal cuff to interact with the wall of the body vessel at the proximal end of the defect; positioning the distal cuffs to interact with the wall of the body vessel at the distal end of the defect; and allowing the bodily fluids in the body vessel to contact and interact with the cuffs. The absorption of water by the polyurethane hydrogel causes the cuffs to expand in diameter by about 10-30%, thereby, exerting a sealing force between the cuff and the wall of the body vessel.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

FIG. 2A is a graphical representation of a modular stent-graft made according to the teachings of the present disclosure used to repair an abdominal aortic aneurysm (AAA) shown in the condition as initially inserted into the body vessel;

FIG. 2B is a graphical representation of the modular stent-graft of FIG. 2A shown in the condition that occurs after being exposed to the aqueous environment of the body vessel;

DETAILED DESCRIPTION

Figure 1B:
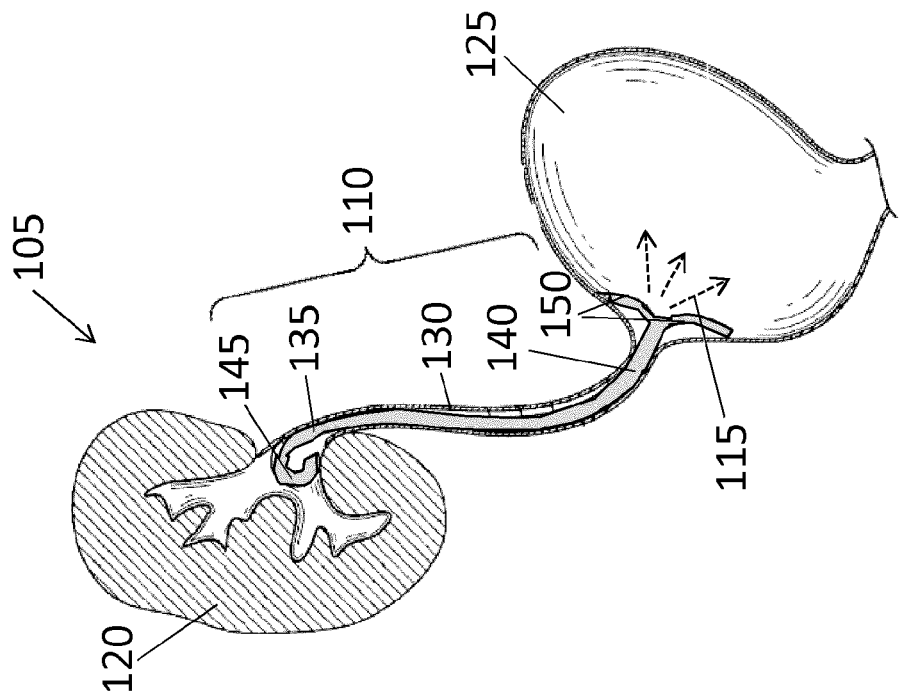
FIG. 1B is a graphical representation of a conventional unibody stent-graft used to provide urinary drainage between the kidney and bladder.

The following description is merely exemplary in nature and is in no way intended to limit the present disclosure or its application or uses. It should be understood that throughout the description and drawings, corresponding reference numerals indicate like or corresponding parts and features.

The present disclosure generally provides a stent-graft for insertion into a body vessel for use either alone or with a branch connection device. The stent-graft of the present disclosure exhibits an enhanced ability to maintain its original position when placed into a patient and resist the potential of migration without causing excessive discomfort to the patient. According to the teachings of the present disclosure, this stent-graft is capable of exerting a sealing or anchoring force against the wall of the body vessel. Such a stent-graft can overcome many of the problems associated with conventional stent-grafts as currently used in many different applications, for example, endovascular repair and ureteral drainage.

Figure 1A:
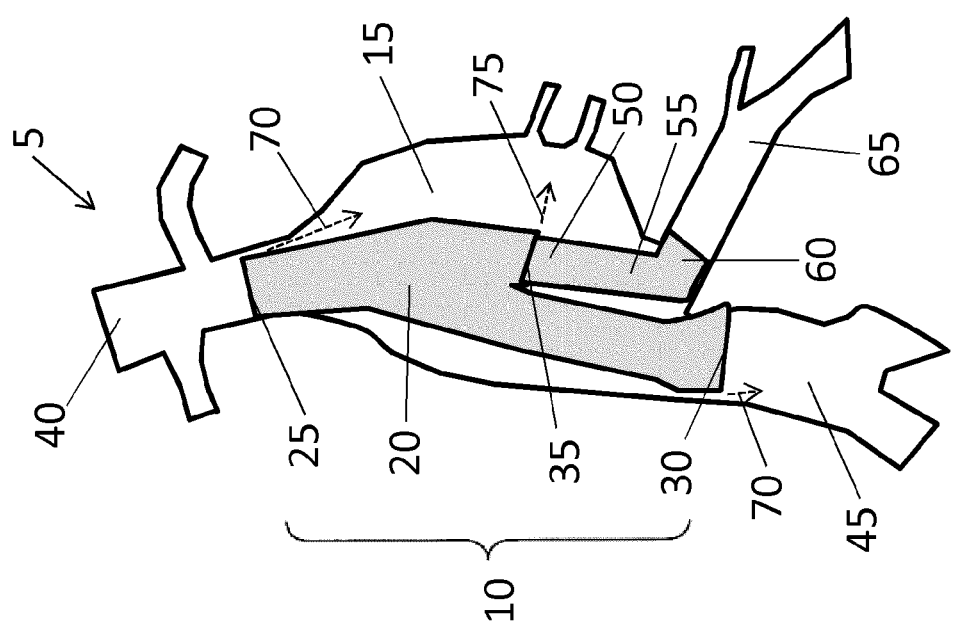
FIG. 1A is a graphical representation of a conventional modular stent-graft used to repair an abdominal aortic aneurysm (AAA)

Referring to FIG. 1A, a body vessel 5 is shown where a conventional modular stent-graft 10 is used to repair an abdominal aortic aneurysm (AAA) 15. This conventional stent-graft 10 consists of a bifurcated main stent body 20 having a single proximal end portion 25 and a first distal end portion 30 and a second distal end portion 35. The proximal end portion 25 and the first distal end portion 30 contacts and interact with the proximal end 40 and distal end 45 of the main body vessel 5, respectively. The second distal end portion 35 is positioned to connect with the proximal end portion 50 of a second stent-graft 55. The second stent-graft 55 may be a unibody stent graft 55 whose distal end portion 60 interacts with a branch 65 associated with the body vessel 5. The use of this type of modular graft-stent 10 can lead to the occurrence of leakage from the intersection of the graft-stent 10 with the wall of the body vessel 5 as indicated by the arrows 70. Further leakage may arise from misalignment of the connection made between the main stent body 20 and the second stent-graft 55 as indicated by the arrow 75.

Referring to FIG. 1B, a body vessel 105 is shown where a conventional unibody stent-graft 110 is used to provide urinary drainage 115 from the renal pelvis of the kidney 120 into the bladder 125. This conventional stent-graft 110 is comprised of a long tubular body 130 having a proximal end portion 135 and a distal end portion 140. The proximal end portion 135 further includes a pigtail loop 145, while the distal end portion includes a double-J pattern with oppositely directed loops 150. The pigtail loop 145 and double-J loops 150 are used to minimize migration of the stent-graft 110 from its originally established position. However, the cost of this migratory mitigation measure is considerable discomfort encountered by the patient.

Figure 3:
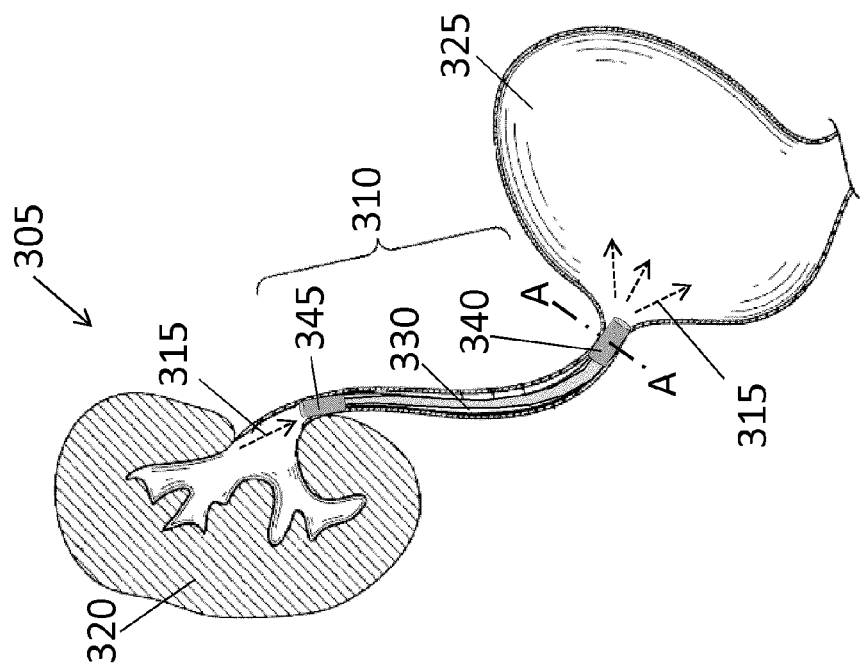
FIG. 3 is a graphical representation of a unibody stent-graft made according to the teachings of the present disclosure used to provide urinary drainage shown in the condition that occurs after being exposed to the aqueous environment of the body vessel.

The stent-graft of the present disclosure can reduce or overcome the problems encountered when using conventional stent-grafts 10, 110 as described above. Referring to FIGS. 2A, 2B, and 3, a modular stent-graft 210 and a unibody stent-graft 310 made according to the teachings of the present disclosure is provided. In FIGS. 2A and 2B, the modular stent-graft 210 is shown in the context of repairing an abdominal aortic aneurysm (AAA) 215 in a body vessel 205.

The modular stent-graft 210 comprises a proximal cuff 225, a main elongated body 220, a first distal cuff 230, and a second distal cuff 235. In FIG. 2A, the main elongated body 220 is shown to be bifurcated into two extensions 221, 222 with one extension 221 directed towards the distal end 245 of the main body vessel 205 and one extension 222 directed towards the distal end 265 of a branch arising from the main body vessel 205. Each of the extensions 221, 222 ends at a distal cuff 230, 235. The proximal cuff 225 is directed towards the proximal end 240 of the body vessel 205.

The proximal cuff 225 and the distal cuffs 230, 235 of the bifurcated stent-graft 210, when initially inserted into the body vessel 205, each have an outer diameter that is the same or similar to the outer diameter of the elongated body 220. One skilled-in-the-art will understand that the modular stent-graft 210 may comprise more than two distal cuffs depending upon the number of branches present in the body vessel 205. The elongated body 220 has a greater longitudinal length than either the proximal 225 or distal 230, 235 cuffs.

The second distal cuff 235 is positioned to contact the proximal end 250 of a second stent-graft 255. The second stent-graft 255 may be a unibody stent graft 255 whose distal end may also include a distal cuff 260 that interacts with a branch 265 associated with the body vessel 205. One skilled-in-the-art will understand that the second stent-graft 255 may also be a modular in nature depending upon the number of branches in the body vessel 205 that need to be addressed.

A hydrophilic polyurethane hydrogel is disposed about at least one of the proximal 225 and distal cuffs 230,235 of the stent-graft 210. Preferably, the proximal cuff 225 includes the hydrophilic polyurethane hydrogel. According to another aspect of the present disclosure, all of the cuffs 225, 230, 235, 260 preferably include the polyurethane hydrogel. When initially inserted into the body vessel 205, each of the cuffs 225, 230, 235 and the elongated body 220 are similar in diameter and allow for continued fluid flow 270 around the exterior of the stent-graft 210. However, as shown in FIG. 2B, upon exposure to an aqueous environment (i.e., bodily fluids) the polyurethane hydrogel expands so that the outer diameter of the cuffs 225, 230, 260 become greater than the outer diameter of the proximal end 240, distal end 245, or branch 265 of the body vessel 205. This increase in diameter causes the cuffs 225, 230, 260 to exert a sealing force against the wall of the body vessel 205. This sealing force stops the bodily fluid from flowing between the cuffs 225, 230, 260 and the vessel wall, thereby, forcing all of the fluid flow 270 to enter and exit through the stent-graft 210.

In FIG. 3, a unibody stent-graft 310 made according to one aspect of the present disclosure is shown in a body vessel 305 providing urinary drainage 315 from the renal pelvis of the kidney 320 into a bladder 325. This unibody stent-graft 310 comprises a proximal cuff 345, a main elongated body 330, and a distal cuff 340. A hydrophilic polyurethane hydrogel is disposed about at least one of the proximal 345 and distal cuffs 340 of the stent-graft 310. Preferably, the proximal cuff 345 or both the proximal cuff 345 and distal cuff 340 includes the hydrophilic polyurethane hydrogel.

When initially inserted into the body vessel 305, each of the cuffs 340, 345 and the elongated body 330 are similar in diameter, thereby, allowing for the possibility of urine reflux around the exterior of the stent-graft 310. However, as shown in FIG. 3, upon exposure to an aqueous environment (i.e., bodily fluids) the polyurethane hydrogel expands so that the outer diameter of the cuffs 340, 345 become greater than the outer diameter of the elongated body 330 and interact with the wall of the body vessel 305. This increase in diameter causes the cuffs 340, 345 to exert a sealing force against the wall of the body vessel 305. This sealing force stops the urinary drainage from flowing between the cuffs 340, 345 and the vessel wall, thereby, forcing all of the flow 315 to enter and exit through the stent-graft 310. One skilled-in-the-art will understand that the use of cuffs 340, 345 may take the place of or be used in addition to any known conventional means of securing a stent-graft in a body vessel, including but not limited to a pigtail loop 145 and double-J loops 150.

Figure 4:
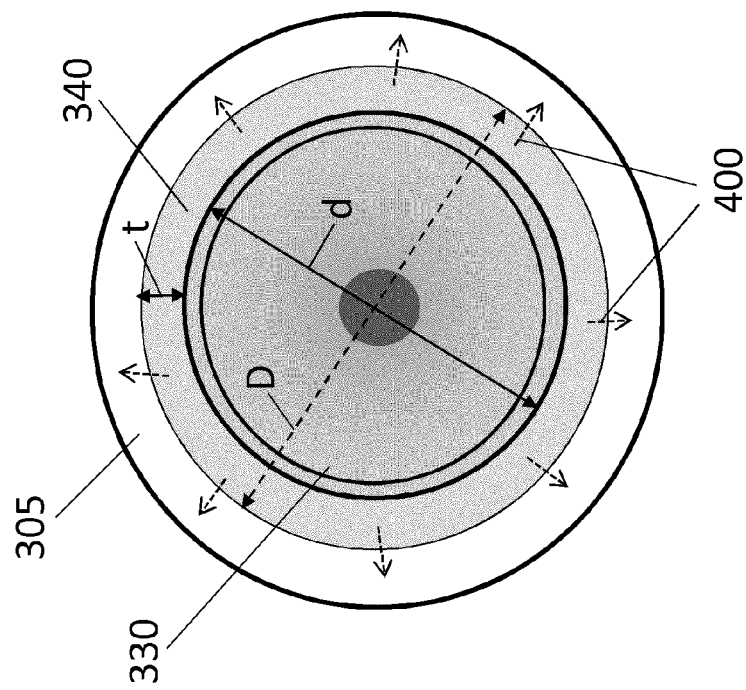
FIG. 4 is a cross-sectional view of the unibody stent-graft of FIG. 3 taken along the axis A-A.

Referring now to FIG. 4, a cross-sectional view of the unibody stent-graft 310 is shown projected along axis A-A. The stent-graft 310 is shown in its fully expandable state to be comprised of an inner elongated body 330 and a cuff 340 of an expanded or swollen polyurethane hydrogel. The expanded cuff 340 exerting a sealing force 400 against the wall of the body vessel 305. The thickness (t) of the cuff 340 is predetermined based upon the inner diameter (D) of the body vessel 305 and the outer diameter (d) of the elongated body 330. The thickness (t) of the cuff 340 should be capable of exerting a sealing force 400 against the inner wall of the body vessel 305 when the polyurethane hydrogel of the cuff 340 swells due to being exposed to the aqueous fluid present in the body vessel 305. The overall length of the cuff 340 is also predetermined and selected to provide an effective seal against leakage of any body fluid between the cuff 340 and the wall of the vessel 305. Thus the thickness (t) and length of the cuff may be varied depending upon the intended application and parameters associated with the body vessel 305 and elongated body 330 of the stent-graft 310.

Figure 5B:
FIG. 5B is a perspective view of the stent-graft of FIG. 5A demonstrating the flexibility of the stent-graft.
Figure 5A:
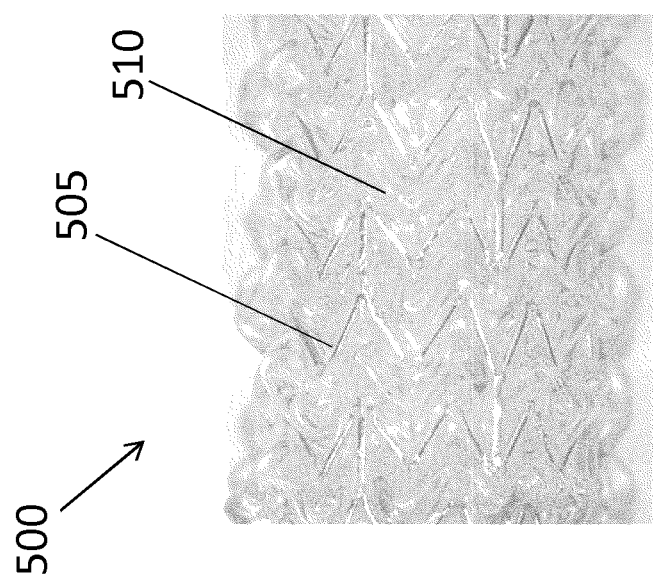
FIG. 5A is a perspective view of a stent-graft comprised of an expandable coil structure embedded in a polyurethane hydrogel according to one aspect of the present disclosure.

The use of a hydrophilic polyurethane hydrogel can potentially reduce the incidence of encrustation and the occurrence of a complicating infection. Hydrophilic polyurethanes can be applied as cuffs to existing medical devices, such as a Zilver® drug eluding stent, Zenith® endovascular grafts, and ureteral stents, to enhance their functionality. Typically, a stent-graft will exhibit undesirable stiffness due to the struts of the stent-graft structure being constrained by a polymer layer. However, if this polymer layer is a polyurethane hydrogel, the polymer layer will enlarge or swell when exposed to an aqueous environment, thereby, allowing the struts of the stent-graft to bend more freely without kinking. An example of a stent-graft 500 having an expandable structure 505 embedded in a polyurethane hydrogel layer 510 is shown in FIGS. 5A and 5B. Such a stent-graft 500 is found to be capable of being easily being bent or shaped.

The polyurethane hydrogel layer represents a 3-dimensional network of cross-linked hydrophilic macromolecules that can swell and absorb about 20 to 90 percent by weight of water. The hydrogel layer may be applied as or onto the cuff of a stent-graft by coating, adhesive bonding, lamination, extrusion, or molding. The application method used is selected to provide a layer of the hydrogel having a substantially uniform thickness.

Figure 7A:
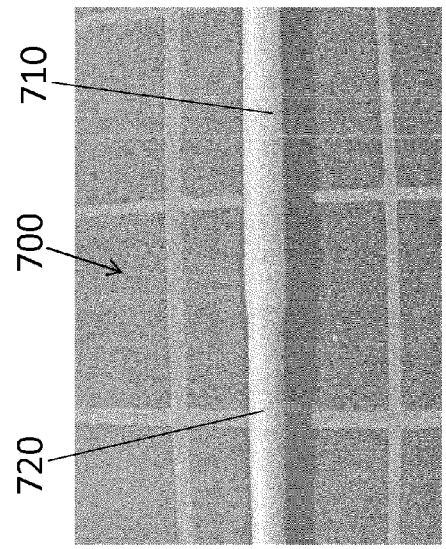
FIG. 7A is a perspective view of a stent-graft prepared according to one aspect of the present disclosure with a polyurethane hydrogel cuff in a "dried" condition.
Figure 6A:
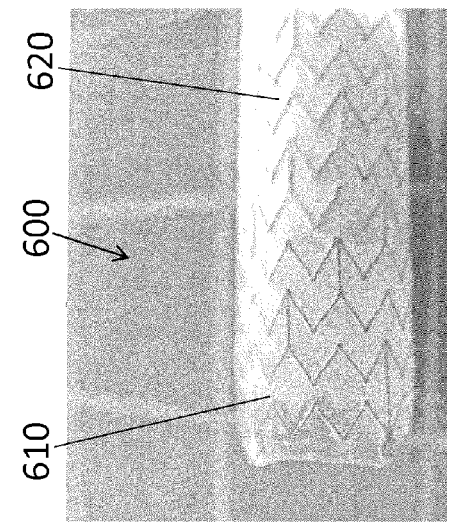
FIG. 6A is a perspective view of a stent-graft prepared according to one aspect of the present disclosure with a polyurethane hydrogel cuff in a "dried" condition.

The stent-graft 600, 700 may be comprised of an expandable structure embedded within a polymeric matrix as shown in FIG. 6 or a solid polymeric matrix as shown in FIG. 7. In both cases, the polyurethane hydrogel may be applied as a strip or band disposed around the outer surface of the cuff 610, 710. Referring to FIGS. 6A and 7A, after the hydrogel is disposed around the cuff 610, 710 of a stent-graft 600, 700, it may be dried by any method known in the art, including but not limited to conduction drying, convection drying, hot air impingement, steam treatment, infrared irradiation, ultraviolet irradiation, and microwave irradiation. Preferably, the hydrogel coating is dried by the application of thermal energy. A stent-graft 600, 700 whose hydrogel cuff 610, 710 is dried represents the stent-graft in a condition ready for insertion into a body vessel. In this condition, the hydrogel cuff 610, 710 is shown to exhibit about the same diameter as the elongated body 620, 720 of the stent-graft 600, 700.

Figure 7B:
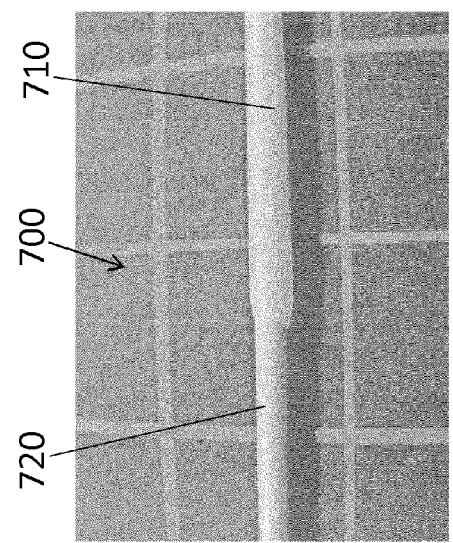
FIG. 7B is a perspective view of the stent-graft of FIG. 7A after exposure to an aqueous environment.
Figure 6B:
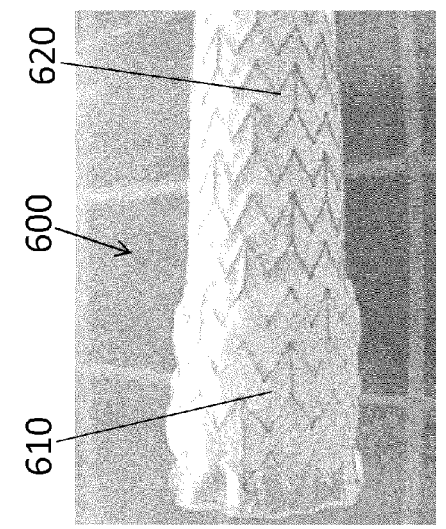
FIG. 6B is a perspective view of the stent-graft of FIG. 6A after exposure to an aqueous environment.

Upon exposure to an aqueous environment, i.e., bodily fluid, the cuff 610, 710 of the stent-graft 600, 700 will absorb water and swell as shown in FIGS. 6B and 7B to a diameter that is larger than the diameter of the elongated body 620, 720. In FIG. 7A, the outer diameter of the cuff 710 and elongated body 720 of the stent-graft 700 in the "dried" condition was measured to be 2.17 mm. Upon exposure of the stent-graft 700 to an aqueous environment, the cuff 710 of the stent-graft 700 was measured to expand to an outer diameter of 2.47 mm, while the elongated body 720 remained unchanged. This increase in diameter of the cuff 710 represents and expansion of about 14%. The increase in diameter of a cuff 710 comprising a polyurethane hydrogel upon exposure to an aqueous environment can be on the order of about 10% to 30%.

The hydrophilic polyurethane hydrogel can be applied to new stent-grafts as part of their manufacturing operation or applied to stent-grafts that have already been manufactured. In this latter case, the hydrogel may be applied as a cuff to the surface of a balloon/self-expandable covered stent or any other stent design. One skilled in the art will also understand that the polyurethane hydrogel of the present disclosure may also be used as the base polymer from which the stent is extruded.

According to another aspect of the present disclosure, the hydrophilic polyurethane hydrogel may be used to replace the base polymer present in a ureteral stent-graft. The swelling properties of the hydrogel will allow one to extrude the material to form a stent-graft with a smaller diameter than necessary to perform the ureteral application. After implantation the stent-graft will swell to the desired size providing a proper fit in the body vessel. For example, if a 9-French diameter (3 mm) ureteral stent-graft is desired, a 6-French (2 mm) diameter stent-graft could be extruded using a polyurethane hydrogel. After implantation the stent-graft would swell to the desired 9-French diameter and become both lubricious and more flexible. This type of stent-graft may reduce the irritation and inflammation associated with conventional ureteral stenting, thereby, being more comfortable to the patient. This type of stent-graft may also reduce the occurrence of urine reflux, thereby, minimizing the potential development of sepsis or other infection. In other words, the swelling of the stent-graft to provide a proper fit with the body vessel reduces the possibility that urine may travel from the bladder into the ureter or kidney. Since a polyurethane hydrogel can be extruded at a lower temperature than a conventional polyurethane material, the polyurethane hydrogel could be loaded with a therapeutic agent prior to extrusion because the therapeutic agent would be capable of avoiding degradation during the extrusion process.

The shape of the stent-graft may be predetermined according to the application or, more specifically, by the location of the implantation sites both proximal and distal to the area that is to be bridged by the stent-graft. When the aneurysm arises at the intersection of key branches in the body vessel, the stent-graft will have to accommodate the branched shape. The stent-graft may be un-branched, i.e., a single lumen connects to one proximal orifice and one distal orifice, bifurcated, i.e., a single lumen connects to one proximal orifice and is then divided to connect to two distal orifices, or multi-branched, i.e., a single lumen connects to one proximal orifice and is then divided to connect to multiple distal orifices.

The stent-grafts according to one aspect of the present disclosure may be either unibody or modular in nature. In a unibody stent-graft since there is no interconnections between multiple components, there is no possibility of component separation or intercomponent leakage as there is with a modular stent-graft. However, the insertion of a unibody stent-graft with multiple branches is more difficult in that it requires the insertion and use of a system of catheters and wires. Modular stent-grafts on the other hand are more versatile, flexible, and simpler to implant, as well as providing an opportunity to make dimensional adjustments in situ.

The main body of the stent-graft may be made from any biocompatible material that will allow for connective tissue in-growth and be impervious enough to prevent bleeding. Examples of such materials include, but are limited to, polytetrafluoroethylene (PTFE), silicones, polyurethane-latex, polyolefins, vinyl aromatic polymers, polyesters, and mixtures, blends, or copolymers thereof. The biocompatible material may be woven into a fabric with any differences in wall thickness reflecting the use of a smaller diameter fiber, e.g., Dernier size, and possibly a tighter weave to limit porosity. The biocompatible material may also be used to encase a Nitinol or another metallic stent core. Preferably, the biocompatible material is resiliently deformable to conform readily to the predetermined curvature dictated by the intended application.

The stent-graft may comprise an expandable mesh upon which the polyurethane hydrogel is applied and disposed within the interstices of the mesh. This expandable mesh can be made from braided filaments, a coiled spring, or any other expandable arrangement that may be collapsed and when released expands radially. The expandable mesh may be made from any suitable material, such as stainless steel, tantalum, gold, titanium, and Nitinol. The expandable mesh should be designed such that it will have exhibit approximately the same or similar expansion ratio as the polyurethane hydrogel that is utilized in order to allow for full expansion with minimum resistance.

Prior to the application of the polyurethane hydrogel to the stent-graft, the surface of the stent-graft may be activated through the use of known techniques, such as plasma treatment or chemical treatment. Preferably, the surface of the stent-graft is treated with a source of nitrogen atoms in order to form amino functionality on said surface. The use of a combination of oxidative chemical or plasma treatments followed by exposure to nitrogen-containing plasma gases, ammonia, or low boiling amines may be utilized.

The polyurethane hydrogel may optionally include a therapeutic agent to reduce or prevent restenosis or clotting at the site of implantation. The therapeutic agent may be an anti-platelet, anti-coagulant, anti-betabolite, anti-aniogenic, anti-thrombogenic, or anti-proliferative drug.

The exterior of the stent-graft may optionally comprise one or more radiopaque or echogenic features, such as a marker used to detect positioning of the stent-graft via a suitable imaging technique. The radiopaque or echogenic feature may be applied by any fabrication method or absorbed into or sprayed onto the surface of the stent-graft. Common radiopaque materials include barium sulfate and zirconium dioxide, as well as various elements, such as cadmium, tungsten, gold, tantalum, bismuth, platinum, iridium, and rhodium.

The stent-graft may be varied in both length and diameter depending upon the intended application. Ureteral stent-grafts may be on the order of about 3-30 cm in length, and have a diameter of about 1.5-6.0 mm (0.06-0.20 inch) in diameter. A stent-graft used for repairing a ruptured abdominal aorta aneurysm may be on the order of about 12-34 mm in diameter and up to about 100 mm in length.

Figure 8:
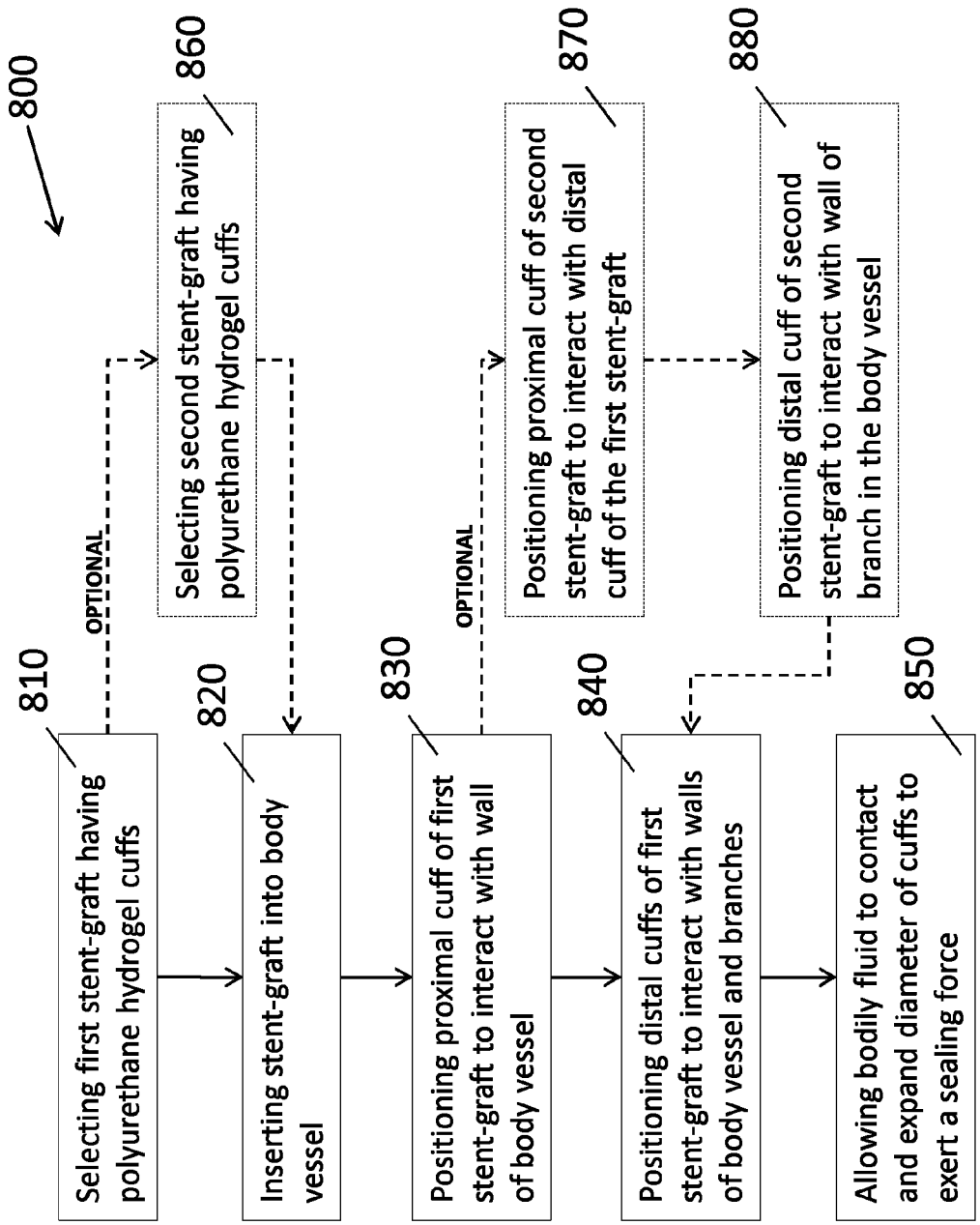
FIG. 8 is a graphical representation of a method for repairing a ruptured or symptomatic defect in a body vessel having bodily fluids using a stent-graft.

Another objective of the present disclosure is to provide a method of repairing a ruptured or symptomatic defect in a body vessel having bodily fluids using a stent-graft. The method 800 as described in FIG. 8 generally comprises the first step of selecting 810 a first stent-graft that has a radially expandable cylindrical body. This cylindrical body comprises a proximal cuff, an elongated main body, and a number of distal cuffs predetermined by the number of branches arising from the defect that are desired to be addressed. The proximal cuff and distal cuffs of this first stent-graft each have a "dried" polyurethane hydrogel layer disposed about it.

The method further comprises the steps of inserting 820 the first stent-graft into the body vessel; positioning 830 the proximal cuff of the first stent-graft to interact with the wall of the body vessel at the proximal end of the defect; positioning 840 the distal cuffs of the first stent-graft to interact with the wall of the body vessel at the distal end of the defect and at the predetermined number of branches arising from the defect; and finally allowing 850 the bodily fluids in the body vessel to contact and interact with the cuffs of the first stent-graft. The absorption of water by the polyurethane hydrogel causes the cuffs to expand in diameter, thereby, exerting a sealing force between the cuff and the wall of the body vessel.

Depending upon the type of defect, the method may optionally comprise the additional steps of selecting 860 a second stent-graft that has a radially expandable cylindrical body. This body also comprises a proximal cuff, an elongated main body, and a distal cuff. In the second stent-graft, the distal cuff has a "dried" polyurethane hydrogel layer disposed about it. The proximal cuff of the second stent-graft is then positioned 870 to interact with the distal cuff of the first stent-graft, while the distal cuff of the second stent-graft is positioned 880 to interact with the wall of the body vessel at a branch arising from the defect.

The step of selecting 810 a first stent-graph may include the selection of one from the group of a modular stent-graft and a unibody stent-graft. When desirable, the proximal cuff, elongated body, and distal cuff of the stent-graft may be extruded from a polyurethane hydrogel.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A stent-graft for insertion into a body vessel for use alone or with a second stent-graft capable of exerting a sealing or anchoring force against the wall of the body vessel, the stent-graft comprising:

a radially expandable cylindrical body having a proximal cuff, an elongated body, and a distal cuff, the elongated body having a substantially similar outer diameter, the elongated body having greater longitudinal length than the proximal and distal cuffs; and a hydrophilic polyurethane hydrogel layer disposed about at least one of the proximal and distal cuffs, the polyurethane hydrogel layer having a pre-dried condition, the cuff with the polyurethane hydrogel layer disposed about it having the same outer diameter as the elongated body in the pre-dried condition;

wherein upon exposure to an aqueous environment, the pre-dried polyurethane hydrogel layer expands so that the outer diameter of the cuff is greater than the outer diameter of the elongated body to exert a sealing force against the wall of the body vessel, wherein the pre-dried polyurethane hydrogel layer is disposed to expand between 10-30% larger than the outer diameter of the elongated body to provide a proper fit in the body vessel to reduce irritation and inflammation.

2. The stent-graft of claim 1, wherein the expandable cylindrical body further comprising more than one distal cuff in order to address the occurrence of a branch in the body vessel.

3. The stent-graft of claim 1, wherein the expandable cylindrical body is one selected from the group of a modular stent-graft and a unibody stent graft.

4. The stent-graft of claim 1, wherein the polyurethane hydrogel layer is applied as a cuff on the cylindrical body using a method selected from the group of coating, adhesive bonding, lamination, extrusion, or molding.

5. The stent-graft of claim 4, wherein the polyurethane hydrogel layer is applied with a substantially uniform thickness (t).

6. The stent-graft of claim 1, wherein the elongated body is made from one selected from the group of polytetrafluoroethylene (PTFE), silicone, polyurethane-latex, polyolefin, vinyl aromatic polymer, polyester, and a mixture or copolymer thereof.

7. The stent-graft of claim 1, wherein the proximal cuff, distal cuff, and elongated body are extruded from a polyurethane hydrogel.

8. The stent-graft of claim 1, wherein the polyurethane hydrogel is disposed around all of the cuffs.

9. The stent-graft of claim 6, wherein the elongated body further comprises an expandable mesh.

* * * * *